United States Patent [19]

Weber

[11] Patent Number: 4,913,642

[45] Date of Patent: Apr. 3, 1990

[54] MOLD FOR FORMING ASYMMETRIC BALLOON

[75] Inventor: Roland E. Weber, Minnetonka, Minn.

[73] Assignee: Applied Biometrics, Inc., Minnetonka, Minn.

[21] Appl. No.: 324,241

[22] Filed: Mar. 15, 1989

Related U.S. Application Data

[62] Division of Ser. No. 210,718, Jun. 23, 1988.

[51] Int. Cl.[4] .................... B28B 21/46; B29C 49/30
[52] U.S. Cl. .................... 425/275; 249/180; 249/184; 425/522; 425/538
[58] Field of Search ....... 428/275, 269, 470, DIG. 58; 249/180, 184; 425/DIG. 57, 522, 538

[56] References Cited

U.S. PATENT DOCUMENTS

| | | | |
|---|---|---|---|
| 2,100,576 | 11/1937 | Spanel | 425/275 |
| 2,238,833 | 4/1941 | Tillotson | 425/269 |
| 2,328,769 | 9/1943 | Aazin | 425/269 |
| 2,568,128 | 9/1951 | Morris | 425/269 |
| 2,614,293 | 10/1952 | Vaisala | 425/269 |
| 2,830,325 | 4/1958 | Bray | 249/134 |
| 2,952,094 | 9/1960 | Ebel | 425/275 |
| 4,501,545 | 2/1985 | Divoky | 425/275 |
| 4,607,643 | 8/1986 | Bell et al. | 128/715 |
| 4,671,295 | 6/1987 | Abrams et al. | 128/661 |
| 4,700,700 | 10/1987 | Eliachar | 128/207.15 |

Primary Examiner—Jay H. Woo
Assistant Examiner—K. P. Nguyen
Attorney, Agent, or Firm—Vidas & Arrett

[57] ABSTRACT

Blood flow in the aorta and pulmonary artery of a mammal, most typically a human, is measured volumetrically by a non-invasive, ultrasound apparatus. The apparatus (10) includes a tracheal tube or probe with of flexible tubing (11) having a transducer assembly (21) mounted at one end the tube. The transducer assembly (21) is disposed to transmit ultrasound in selected directions. Electrical conductors (24) extend the length of the probe from the transducer assembly. Improved means is provided to positively locate the probe in the trachea and to urge the ultrasound transducer assembly (21) into intimate contact with the inner wall of the trachea. The improved location and urging means comprises a single inflatable asymmetric balloon cuff member (29) mounted on the tube (11) in proximity to and above the transducer assembly (21) and extending around the entire periphery of the tube, the balloon being mounted on the tube such that when inflated the balloon sealingly engages the tracheal wall while urging the transducer assembly into contact with the inner wall of the trachea.

The asymmetric balloon cuff is conveniently formed in a mold prepared by angularily sectioning the conical portion if a pair of funnel shaped mold forms at equal angles relative to the central axis thereof, rotating one of the sectioned funnel forms 180° about the axis and then joining the two forms at the section plane to form the balloon cuff mold form.

4 Claims, 2 Drawing Sheets

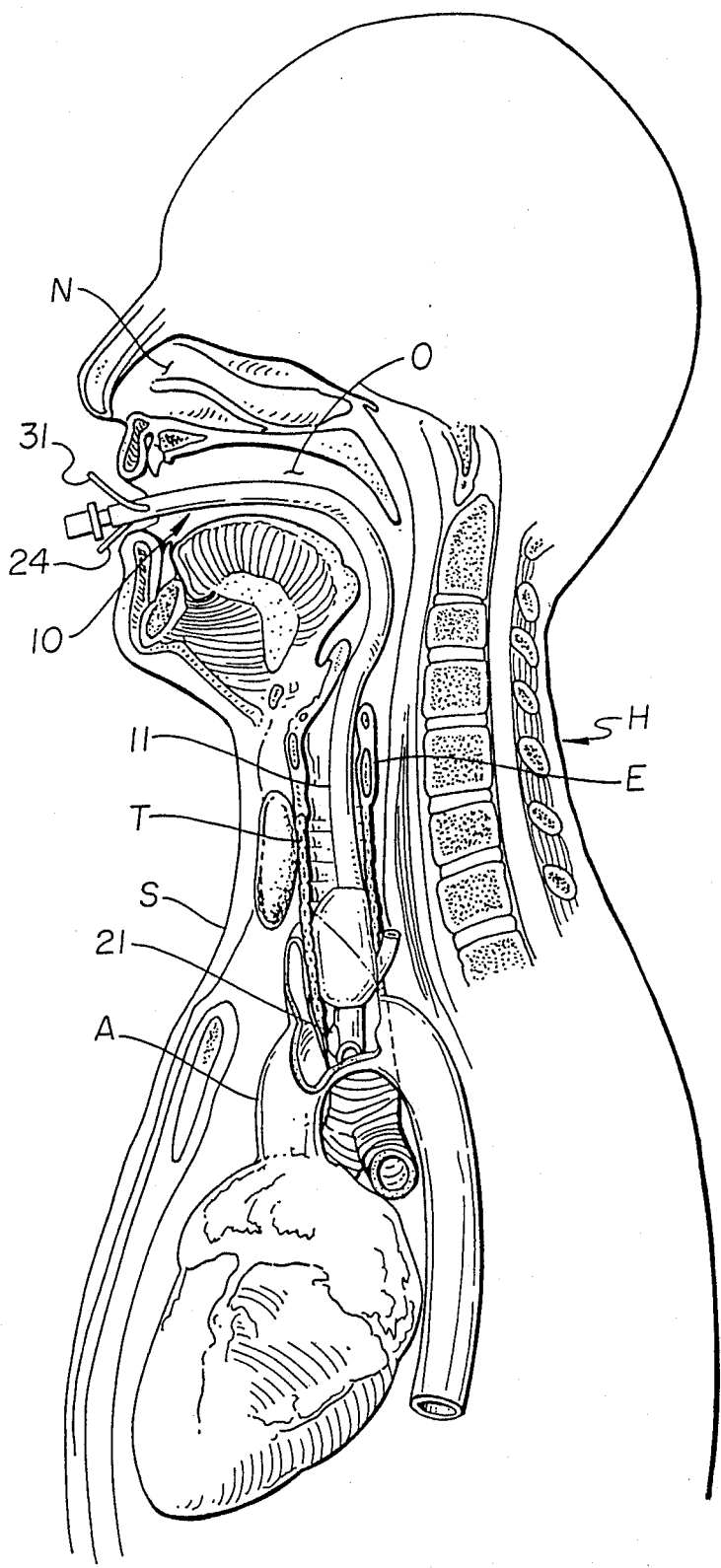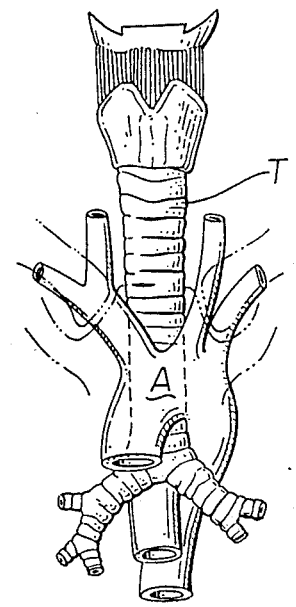
Fig. 1
Fig. 2

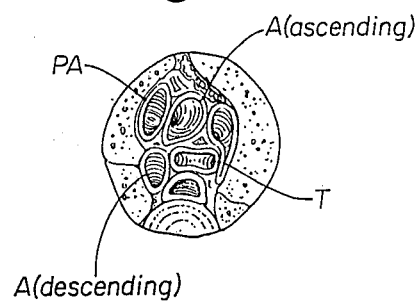
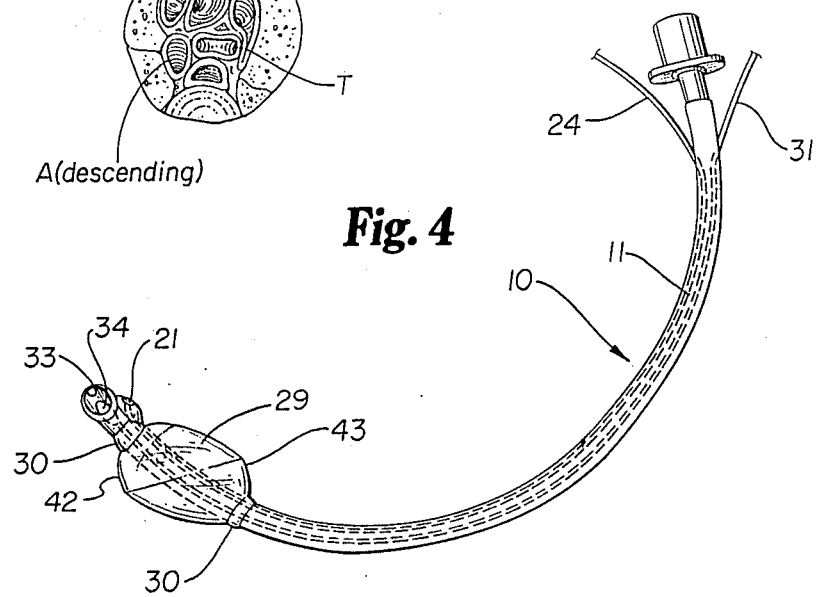
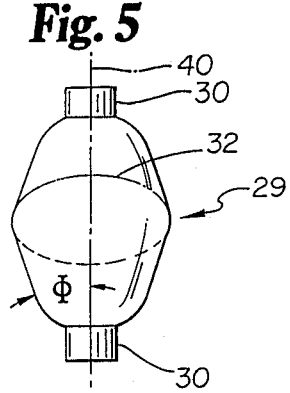
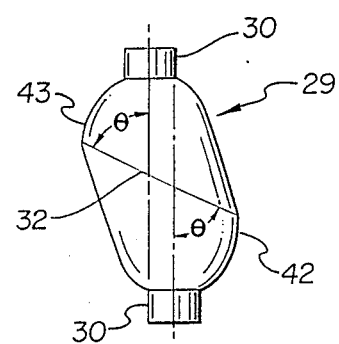
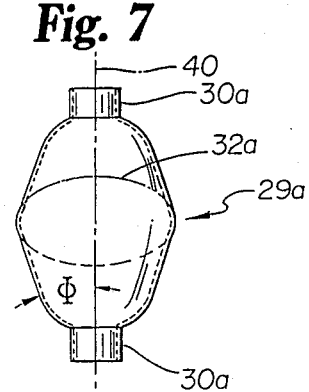
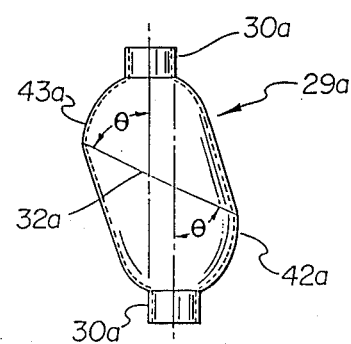

MOLD FOR FORMING ASYMMETRIC BALLOON

This is a divisional of co-pending application Ser. No. 07/210,718 filed on Jun. 23, 1988.

BACKGROUND OF THE INVENTION

1. Field of Invention

Measurement of cardiac output is crucial in the care of critically ill patients such as patients with multiple trauma, patients in overwhelming sepsis, and patients with acute myocardial infarction. In the case of patients with acute myocardial infarction, there is a worsening prognosis with decrease in cardiac output. Knowledge of the cardiac output provides information useful in determining the clinical state of a given patient and in rationally planning therapy for the patient. Such information is not contained in the usually measured vital signs. For example, a low mean arterial pressure with elevated pulse does not adequately distinguish between cardiogenic and septic shock, the treatments for which are quite different. Consequently, a method that distinguishes between cardiogenic and septic shock would be important in planning appropriate therapy. The measurement of cardiac output, in this case, would provide valuable information that would allow an appropriate diagnosis to be made.

2. Prior Art

The importance of knowing cardiac output has led to many methods for its determination. The most commonly used method in widespread clinical use is thermodilution. In the thermodilution method a catheter is placed into the central venous circulation, usually by percutaneous entry into the internal jugular or subclavian vein. A balloon at the end of the catheter is inflated, and the normal flow of blood is employed to direct the tip of the catheter into the pulmonary artery. Measurement of cardiac output is made by observing the dissipation of a temperature pulse, usually a bolus of iced sterile water or saline solution. As is evident, the method cannot be used without invasion of the vascular tree. Indeed, the catheter is threaded through the heart and the heart valves. Flow direction is not entirely reliable. In certain patients access to the pulmonary artery is impossible. During placement of the catheter cardiac arrhythmias are not uncommon. Other complications include sepsis, thrombosis of the central veins, emboli, and fatal rupture of the pulmonary artery. Other disadvantages of the technique include lack of continuous information about the cardiac output and chance location of the catheter, such as in an unfavorable pulmonary artery branch, with erroneous values for the cardiac output. Analysis of the error inherent in the measurement of blood flow by thermodilution has revealed a standard deviation of 20–30%.

Measurement of cardiac output has also been done by the indocyanine green dye technique, which suffers from several disadvantages. The technique is cumbersome, it requires the placement of an arterial catheter, is not accurate at low levels of cardiac output and is difficult to use for repeated measurements in the same patient. Complications include catheter site hematoma, sepsis from the catheter, thromboses of the artery containing the indwelling catheter, and pseudoaneurysm formation at the site of arterial puncture.

The Fick method is based on the measurement of oxygen consumption. It is best used in awake, alert, stable patients not requiring respiratory support on a ventilator. The method requires invasion of the pulmonary artery in order to obtain samples of mixed venous blood for determination of the oxygen content. Like the indocyanine green dye technique, an arterial catheter must be placed for sampling of arterial blood for oxygen content with the disadvantages mentioned above.

Transcutaneous ultrasound has also been used. Ultrasound transducers are placed externally on the body at the suprasternal notch. Under the most sanguine circumstances, at least 10% of patients cannot have their cardiac outputs measured in this way. Many difficulties with this approach have been reported: repeated measurements may lead to varying location of the sample volume that is scanned, there are changes in the angle of intersection of the ultrasound beam with the axis of the vessel, capability for continuous measurement of the cardiac output is not available, and other major thoracic vessels may interfere with the Doppler ultrasound signals. Further, the method is not feasible in many important clinical settings in which the patients are not cooperative or are in the operating room, where the suprasternal notch may not be accessible.

Because of these difficulties, an implantable, removable Doppler ultrasound device for measurement of the cardiac output has been developed for direct attachment to the aorta. The device requires a major, operative, invasive intervention, such as splitting the sternum or removal of a rib to enter the chest cavity, for placement of the device directly on the wall of the aorta. Removal of the device also requires surgical intervention. If the device were to be lost in a major body cavity, a major surgical procedure would be required.

Measurement of cardiac output by continuous or single breath, gas-washout has been attempted, but is not used in standard clinical medicine. Such methods require many approximations of lung function in modeling the system. Time consuming numerical analysis is required. In one study, measurement of cardiac output in anesthetized patients using argon and freon during passive rebreathing was shown to provide lower cardiac outputs than a simultaneously performed Fick determination. The authors concluded that the method caused significant disturbances of hemodynamics and was therefore not suitable for widespread use.

Indirect measurements include the pulse, blood pressure, and urine output, but these measurements are not specific for cardiac output. For example, in the presence of acute renal failure, urine output cannot be correlated with perfusion of major organs.

In the patent art, Tickner, U.S. Pat. No. 4,316,391 discloses an ultrasound technique for measuring blood flow rate. Colley et al., U.S. Pat. No. 4,354,501, discloses an ultrasound technique for detecting air emboli in blood vessels. Numerous patents disclose catheters or probes, including Calinog, U.S. Pat. No. 3,734,094, Wall, U.S. Pat. No. 3,951,136, Mylrea et al., U.S. Pat. No. Re. 31,377, Perlin, U.S. Pat. Nos. 4,304,239; 4,304,240 and 4,349,031, Colley et al., U.S. Pat. No. 4,354,501 and Furler, U.S. Pat. No. 4,369,794.

U.S. Pat. No. 4,331,156 discloses an esophageal cardiac pulse probe which utilizes a closed end lumen with a pressure transmitting fluid therein to transmit sounds from the heart and lungs to an external transducer.

In U.S. Pat. No. 4,671,295 and 4,722,347 there is described a method and apparatus for measuring cardiac output which comprises placing an ultrasound transducer in great proximity to the ascending aorta of the heart of the mammal by passing a probe carrying the transducer into the trachea and transmitting ultrasound waves from the transducer toward the path of flow of blood in the ascending aorta. The probe can be passed through the nasal or oral cavity, past the epiglottis into the trachea or, in the case of patients who have had a tracheostomy, directly into the trachea through the surgical opening. The reflected ultrasound waves are received by the transducer and the average Doppler frequency difference between the transmitted waves and the reflected waves is measured. The cross-sectional size or area of the ascending aorta at the point of ultrasound reflection is calculated and the volumetric blood flow rate is determined from such measurements. The method and apparatus for measuring cardiac output described in U.S. Pats. No. 4,671,295 and 4,722,347 provides for the determination of the cardiac output in a way that is accurate, noninvasive, continuous, inexpensive and suitable for use in those patients whose cardiac output measurement is most critical.

SUMMARY OF THE INVENTION

The present invention comprises an improvement in the apparatus of U.S. Pat. No. 4,671,295 and 4,722,347. In one embodiment the invention comprises an improved tracheal probe for use in determining blood flow in a major discharge artery, including the pulmonary artery and the aorta, of a mammalian heart, which comprises:
  a. a flexible tube having a length sufficient to extend from the oral or nasal cavity of the mammal or from the surgical tracheal opening through the trachea to the bifurcation thereof,
  b. an ultrasound transducer assembly mounted to the tube in proximity to the distal end thereof, and
  c. means mounted on the tube for urging the transducer into contact with the inner wall of the trachea, the improvement comprising that said urging means comprises a single asymmetric inflatable balloon cuff member in proximity to and above the transducer assembly and extending around the entire periphery of the tube, said single asymmetric balloon being mounted on the tube such that when inflated the balloon sealingly engages the tracheal wall while urging the transducer into contact with the inner wall of the trachea.

In another aspect of the invention the inventive balloon cuff may be used with any device, mounted on a catheter or flexible tube which is inserted into a mammalian body passageway and threaded through the passageway to a point in the body where it is desired that the device mounted on the catheter or flexible tube contact the side wall of the body passageway.

A still further aspect of the invention comprises a method for manufacturing the balloon cuff mold by angularly sectioning the conical portion of a pair of funnel shaped mold forms at equal angles relative to the central axis thereof, rotating one of the sectioned funnel forms 180° about the axis and then joining the two forms at the section plane to produce the balloon cuff mold form.

The asymmetric balloon mold and the balloon molded therefrom are further aspects of the invention.

BRIEF DESCRIPTION OF THE DRAWINGS

FIG. 1 is a front-to-back vertical sectional view of the upper portion of the human body showing the oral cavity and the pathway through the trachea to the bifurcation thereof. The heart is shown in lateral or side view. The tracheal probe of the invention is shown in position in the trachea with the transducer assembly contacting the tracheal wall in proximity to the ascending aorta.

FIG. 2 is a front view of the ascending aorta, the trachea, including the bifurcation thereof, and the esophagus and shows the close relationship between the tracheal and the ascending aorta.

FIG. 3 is a horizontal sectional view of the trunk of a human taken at the level of the tracheal bifurcation and shows the close relationship between the trachea and the ascending and descending aorta and the pulmonary arteries.

FIG. 4 is a perspective view from the left side of the tracheal probe of the present invention with the balloon inflated.

FIG. 5 is a front view of the preferred balloon cuff of the invention.

FIG. 6 is a left side view of the referred balloon cuff of the invention.

FIG. 7 is a front view of a mold form for the preferred balloon cuff of the invention.

FIG. 8 is a left side view of a mold form for the preferred balloon cuff of the invention.

DESCRIPTION OF PREFERRED EMBODIMENT

Reference is made to the disclosure of U.S. Pats. No. 4,671,295 and 4,722,347 for a detailed description of the theory and operation of the tracheal probe and for modifications, not relevant to the present invention, which may be employed. The present disclosure should be considered in conjunction with those two patents to the extent necessary to fully understand the invention.

The apparatus of the preferred embodiment consists of a probe with a piezoelectric transducer mounted at one end and electrical conductors extending the length of the probe for connection to conventional directional pulsed or continuous wave Doppler ultrasound hardware, such as that described by Hartley et al. in the Journal of Applied Physiology, October 1974, and by Keagy et al. in the Journal of Ultrasound Medicine, August 1983. Modifications to the signal output can be made to display blood flow volume rate, aorta or other vessel diameter, blood velocity and other selected displays.

The probe 10 is shown in FIGS. 1 and 6. Probe 10 consists of flexible plastic tubing 11. The length must be sufficient to extend from outside the body to the vicinity of the heart through the trachea, entering either through the nasal or oral cavity or through a surgical opening in the case of patients who have had a tracheotomy. The particular probe shown in FIG. 1 is adapted for oral insertion.

Near the distal end of the probe a transducer assembly 21, suitably comprising one or more piezoelectric transducers and associated lenses, is mounted on the exterior of tubing 11. Transducer assembly 21 is used to collect Doppler data for velocity calculation and to collect data for calculation of the diameter of the artery at the point of velocity measurement. Electrical conductors 24, extend the length of tube 11 for connection of transducer assembly 21 to conventional Doppler ultrasound hardware.

An acoustical gel, such as Aquasonic 100, a trademark of and available from Park Laboratories, Orange, N.J., may be placed on the surface of the transducer assembly to fill in the small, irregular space or spaces between the transducer lens and the trachea that remain because of the irregularly shaped and relatively non-deformable cartilaginous inner surface of the trachea when the lens engages the trachea. Alternatively, a generous application of a conventional lubricant, such as a anesthetic lubricant, commonly used when inserting a tracheal tube can be relied upon to provide whatever gap filling is necessary.

An understanding of the use of the present invention requires some understanding of mammalian anatomy and in particular an understanding of the human anatomy, which is shown in pertinent portion in FIGS. 1, 2 and 3. The apparatus is used by placing the ultrasound transducer assembly 21 in great proximity to the arterial vessel in which blood flow is to be measured, most typically the ascending aorta of a human, without surgery or other invasive techniques. The method relies on the anatomical discovery or fact that the ascending aorta is located adjacent the trachea just above the bifurcation thereof, and that a transducer placed in the trachea can be directed toward the ascending aorta and accurate blood flow measurements made without significant interference. With reference to FIGS. 1, 2 and 3, access to the trachea, T, of a human, H, can be had in accordance with standard medical practice through the nasal cavity, N, or the oral cavity, 0, past the epiglottis, E, and into the trachea, T. Access can also be had through a surgical opening at the suprasternal notch, S, in the case of patients who have had a tracheotomy. The ascending aorta, A, and the pulmonary artery, PA, are located in great proximity to the trachea, T, just above the bifurcation, as best seen in FIGS. 2 and 3.

Consequently, a transducer or transducers placed in the trachea as shown in FIG. 1 can be directed to transmit and receive ultrasound waves through the wall of the trachea and through the wall of the ascending aorta or the pulmonary artery to be reflected by the blood flowing in the selected artery and, due to the movement of the blood, cause a Doppler shift in the frequency of the reflected waves as compared to the frequency of the transmitted waves. The ultrasound waves are also reflected by the near and far walls of the artery and such reflection can be used for diameter measurement of the artery.

Means is provided to positively locate probe 10 in trachea, T, and to urge transducer assembly 21 into intimate contact with the inner wall of the trachea.

The disclosed device of U.S. Pat. No. 4,671,295 and 4,722,347 utilizes a pair of inflatable balloons to properly position the transducer assembly 21 against the wall of the trachea in proximity to the ascending aorta. One such balloon is a donut shaped cuff which positions the probe in the center of the trachea and seals the trachea. A second balloon, located on the back side of the probe behind the transducer assembly, is inflated to urge the transducer assembly against the tracheal wall. This is a complicated construction and it is an object of the invention to simplify the construction by utilizing a single balloon cuff, asymmetrically disposed about the axis of the tube 11 when viewed from the side, to simultaneously seal the trachea, securely position probe 10 in the trachea and urge the transducer assembly 21 against the tracheal wall in proximity to the selected artery.

The asymmetric balloon is designated by the numeral 29 and is shown in detail in FIGS. 4–6. The balloon is made of conventional materials. Suitably it is dip or blow molded. The mold is formed by sectioning a pair of cones, suitably funnel shaped cones, at an acute angle relative to the central axis thereof, rotating one of the cones 180° relative to the other and joining the two cones along the section line. The resulting mold form has the shape of the balloon, shown in FIGS. 5 and 6. The balloon has a pair of sleeves 30 formed by the funnel shaft for mating the cuff over tubing 11 over an opening to an inflation lumen 31 which runs along tube 11. Circumferential line 32 defines the mating edges of the two cones. The angle of the conical section relative to the central axis of the cone is designated $\Theta$ in FIG. 6. The angle of the conical surfaces relative to the central axis of the cone is designated $\Phi$ in FIG. 5. Neither angle $\Theta$ nor angle $\phi$ are critical and the selection of angle will generally be determined by the desirability of complying with industry standards regarding the overall dimensions of trachea sealing balloons. Without limitation, however, angle $\Theta$ may suitably be in the range of 50°–75°, preferably 60°–65° and angle $\Theta$ may suitably be in the range of 10°–30°, preferably about 15°–20°.

As shown in FIG. 5, the preferred balloon when viewed from the front is symmetric about the plane the passing through axis line 40 and perpendicular to the page. Preferably when the balloon is mounted on tube 11 this line of symmetry is aligned with the plane which passes through the central axis of tube 11 and the center of transducer assembly 21. However, the two planes may be offset slighty without departing from the invention hereof.

The asymmetry of the balloon when viewed from the side is such that when inflated the balloon has a bulge 42 on the back side thereof on the portion of the cuff closest to the transducer and a second bulge 43 on the front side of the probe of the portion of the cuff furthest from the transducer.

The structure of balloon 29 allows a single balloon to accomplish the functions of the dual balloon system disclosed in U.S. Pats. No. 4,671,295 and 4,722,347. The use of mated angularly sectioned cones to provide a mold configuration conferring the desired asymmetry in the balloon allows the mold to be prepared very inexpensively. These features provide significant advantages over the dual balloon system of U.S. Pats. 4,671,295 and 4,722,347.

A mold form 29a corresponding to balloon 29 is shown in FIGS. 7 and 8 where the numerals 30a, 21a, 42a and 43a correspond to the elements 30, 32, 42 and 43, respectively, of balloon 29. Suitably, the mold form 29a is formed of a pair of mated funnel sections, members 30a comprising the tubular shafts of the funnels, numerals 42a and 43a designating the sectioned conical portions of the respective funnels, and line 32a defining the line along which the two cones were sectioned and subsequently mated. The interior surfaces of the mated funnel sections are shown in phantom in FIGS. 7 and 8. Optionally, the form 29a may be used either as a dip mold form or as a blow mold form, depending on whether the exterior or the interior of the form is used for molding.

In use probe 10 is placed to locate transducer assembly 21 in the trachea, T, pointing toward the selected artery, suitably as the ascending aorta. The position of probe 10 and transducer assembly 21 can be adjusted until the maximum Doppler shift is obtained and the position can also be checked or confirmed by X-rays to insure placement for optimum data collection. In general, transducer assembly 21 should be located just above the tracheal bifurcation and directed toward the selected artery.

For ventilation purposes it is necessary to seal the trachea. It is also important that the transducer assembly 21 be held in position so that it is not moving about within the trachea while measurements of cardiac output are being taken. Use of a traditional symmetric balloon will force the distal end of the probe away from the wall of the trachea and toward the center thereof, thus requiring a second means for urging the transducer assembly against the tracheal wall. The asymmetric balloon 29, however, complements the natural curvature of tube 10, shown in FIG. 4, so that it effectively seals the trachea and holds the tube in place while simultaneously urging the transducer assembly 21 into acoustic contact with the tracheal wall. Inflation of asymmetric balloon 29 is accomplished with using conventional procedures for inflating an endotracheal tube balloon.

In other respects the endotracheal tube 10 is constructed in accordance with recognized standards for construction of endotracheal tubes. In particular, the distal end suitably is provided with a standard bevel opening 33 and oppositely directed Murphy eye 34 manufactured in accordance with ANSI standards.

After proper placement of probe 10 and connection with the electrical hardware, ultrasound signals are generated and the Doppler shift is measured for velocity calculation and data for calculating the diameter of the artery is also collected. These data are used to determine the volumetric rate of blood flow as set forth in detail in U.S. Pat. No. 4,671,295 and 4,722,347.

A large number of patients who require continuous measurement of cardiac output have significant associated clinical problems. Often such patients have multiple systems organ failure, overwhelming sepsis, significant trauma to many major organ systems, decompensated congestive heart failure, or major myocardial infarction. Such patients often have an endotracheal tube in place because of such problems. For example, in patients having a major surgical procedure, use of general anesthesia requires the presence of an endotracheal tube for the maintenance of the patient's airway. In the case of patients having open heart surgery, an endotracheal tube is often in place for the night following surgery. Patients suffering major trauma are routinely intubated following significant thoracic trauma, significant head injury, or multiple abdominal injuries. Patients in multiple systems organ failure, septic shock, or hemorrhagic shock have endotracheal tubes in place to assist ventilation during acute decompensation and in the immediate resuscitation phase. Patients with significant burn injuries frequently require endotracheal intubation during initial resuscitation, for transportation to a burn center, and for thermal injury to the respiratory system. Patients with decompensated congestive heart failure leading to pulmonary decompensation with pulmonary accumulation of fluid require endotracheal intubation. Such patients may have underlying myocardial infarction, cardiomyopathy, cardiac valvular disease, or chronic congestive heart failure. In many of these examples, stabilization of the cardiovascular system is a prerequisite for removal of the tracheal tube. Consequently, use of an endotracheal probe in accordance with the present invention represents no further invasion of any body cavity. Thus, in the case of patients already having a tracheal tube in place, as well as in patients in which no tracheal tube has been previously placed for other reasons, the present invention provides for measurement of cardiac output at optimum locations without major surgical procedure or invasion of a closed body system. No invasion of a major body cavity, not routinely in communication with the external environment, is required. No major or minor surgical procedure is required. No indwelling foreign body is necessary in the vascular system, a major body cavity, or in a major organ. No dye or radioactive substance is necessary for the measurement to be performed, and no air emboli are introduced. Continuous monitoring is also possible.

While the foregoing description of applicants' invention is directed to measurement of cardiac output in the ascending aorta, measurement of blood flow in the descending aorta, the right pulmonary artery and the left pulmonary artery can also be made with the applicants' apparatus. Moreover, the inventive balloon cuff can also be usefully employed with other devices located on catheters or other flexible tubes and inserted through a tubular body passageway to a point where it is desired that the device contact the wall of the passageway to effectively operate the device. For instance, a balloon cuff of the invention may be used to position the end of a laser angioplasty device of the type disclosed in U.S. Pat. No. 4,685,458 adjacent to a plaque deposit in an artery.

I claim:

1. A mold form for a balloon cuff, said form comprising a pair of mated angularily sectioned cones, each of the two cones being sectioned at an equal acute angle relative to the central axis thereof, the cones being mated along the section lines thereof with one cone rotated 180° about its axis relative to the other.

2. A mold form as in claim 1 in which each of said cone portions has a tubular shaft portion at the apex thereof, each said shaft portion functioning as a form for forming a sleeve on a respective end of said balloon cuff.

3. A mold form as in claim 1 wherein exterior surfaces of said mated angularily sectioned cones form a dip mold.

4. A mold form as in claim 1 wherein the said mated angularily sectioned cones comprise inner surfaces of a hollow mold form and define a cavity for a blow mold.

* * * * *